United States Patent [19]

Trenkle et al.

[11] 4,284,654
[45] Aug. 18, 1981

[54] USE OF 1-HYDROXY-1-ETHYNYL-2,2,6-TRIMETHYL CYCLOHEXANE IN AUGMENTING OR ENHANCING THE AROMA OR TASTE OF FOODSTUFFS

[75] Inventors: Robert W. Trenkle, Bricktown; Braja D. Mookherjee, Holmdel; John B. Hall, Rumson; Robin Kasper, Eatontown; Manfred H. Vock, Locust; Ronald Schreck, Keyport; Edward J. Granda, Englishtown; Joaquin F. Vinals, Red Bank, all of N.J.

[73] Assignee: International Flavors & Fragrances Inc., New York, N.Y.

[21] Appl. No.: 156,677

[22] Filed: Jun. 5, 1980

Related U.S. Application Data

[62] Division of Ser. No. 88,451, Oct. 26, 1979, Pat. No. 4,250,332.

[51] Int. Cl.³ .............................................. A23L 1/226
[52] U.S. Cl. ...................................................... 426/538
[58] Field of Search ........................................ 426/538

[56] References Cited

U.S. PATENT DOCUMENTS

| | | |
|---|---|---|
| 3,887,625 | 6/1975 | Schulte-Elte ............... 426/538 X |
| 3,890,370 | 6/1975 | Buchi ........................ 426/538 X |
| 3,899,597 | 8/1975 | Mookherjee et al. ........... 426/538 |
| 3,923,896 | 12/1975 | Schulte-Elte ............... 426/538 X |
| 3,927,107 | 12/1975 | Schulte-Elte ............... 426/538 X |
| 3,928,456 | 12/1975 | Kovats et al. ............... 426/538 X |
| 3,928,645 | 12/1975 | Mookherjee et al. ........... 426/538 |
| 3,946,078 | 3/1976 | Rautenstrauch et al. ....... 426/538 X |
| 3,956,392 | 5/1976 | de Haan et al. ............. 426/538 X |
| 3,956,393 | 5/1976 | Pittet et al. .............. 426/538 X |
| 3,959,508 | 5/1976 | Pittet et al. .............. 426/538 X |
| 3,975,310 | 8/1976 | Kovats et al. ............... 426/538 X |
| 3,996,296 | 12/1976 | Mookherjee et al. .......... 426/538 X |
| 4,000,329 | 12/1976 | Pittet et al. .............. 426/538 |
| 4,107,209 | 8/1978 | Wilson et al. .............. 426/538 X |
| 4,109,022 | 8/1978 | de Haan et al. ............. 426/538 |
| 4,147,672 | 4/1979 | Schulte-Elte ............... 426/538 |

FOREIGN PATENT DOCUMENTS

627453 11/1949 United Kingdom .

Primary Examiner—Joseph M. Golian
Attorney, Agent, or Firm—Arthur L. Liberman

[57] ABSTRACT

Described is the use of the compound having the structure:

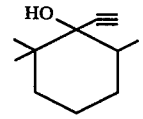

for augmenting or enhancing the aroma or taste of a foodstuff.

1 Claim, 11 Drawing Figures

GLC PROFILE FOR EXAMPLE II.

GLC PROFILE FOR EXAMPLE I.

GLC PROFILE FOR EXAMPLE IV, STEP "A"

GLC PROFILE FOR EXAMPLE III.

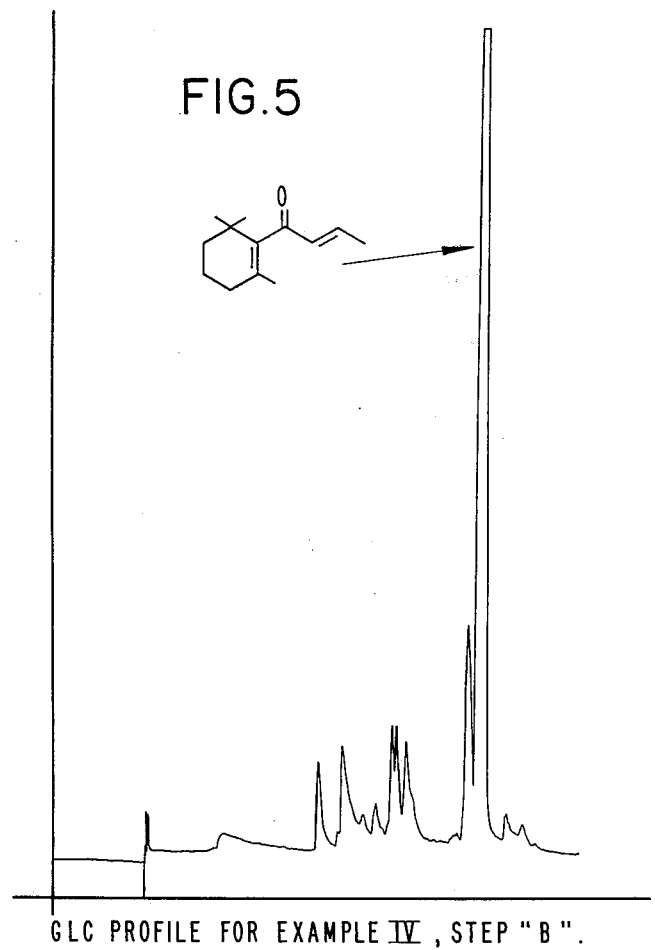
GLC PROFILE FOR EXAMPLE IV, STEP "B".
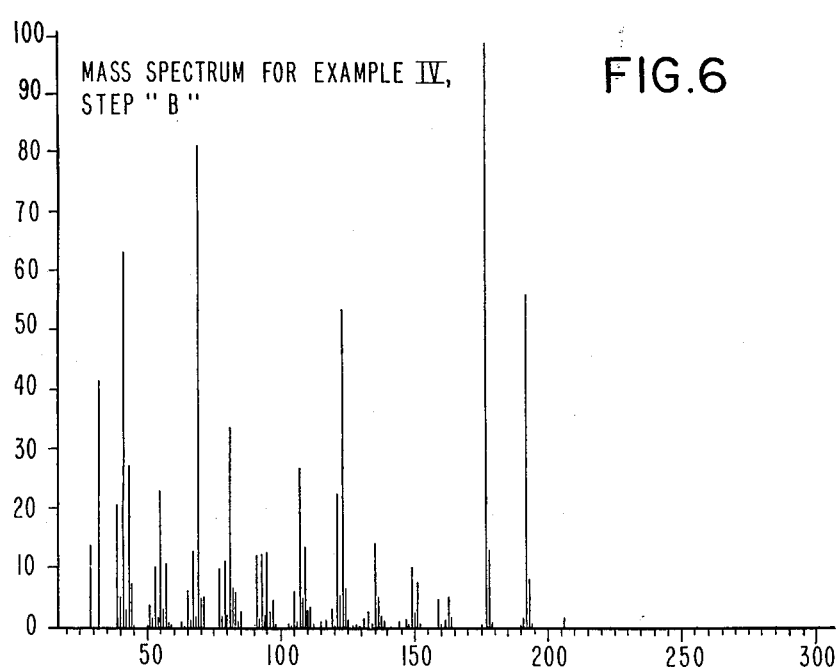
MASS SPECTRUM FOR EXAMPLE IV, STEP "B"

IR SPECTRUM FOR EXAMPLE IV, STEP "B"

NMR SPECTRUM FOR EXAMPLE V.

IR SPECTRUM FOR EXAMPLE V.

MASS SPECTRUM FOR EXAMPLE V.

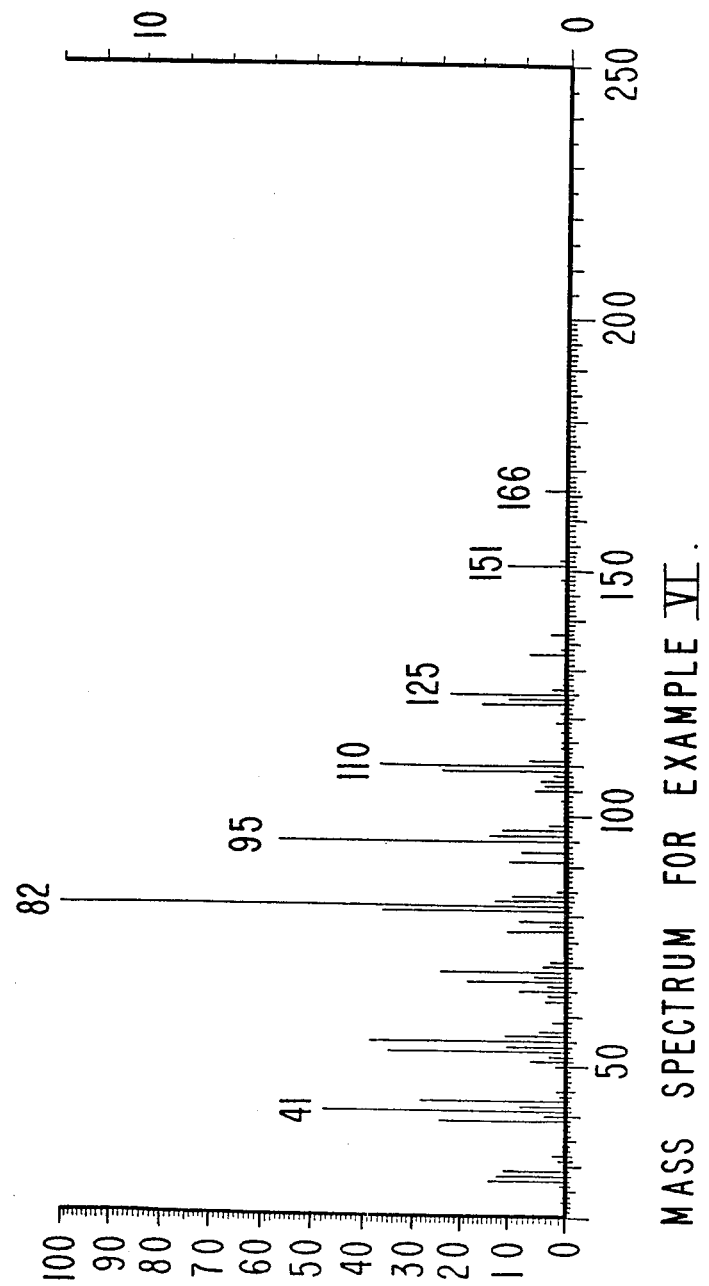

USE OF 1-HYDROXY-1-ETHYNYL-2,2,6-TRIMETHYL CYCLOHEXANE IN AUGMENTING OR ENHANCING THE AROMA OR TASTE OF FOODSTUFFS

This application is a divisional of application for United States Letters Patent Ser. No. 088,451 filed on Oct. 26, 1979, now U.S. Pat. No. 4,250,332 which issue on Feb. 10, 1981.

BACKGROUND OF THE INVENTION

The present invention provides the compound having the structure:

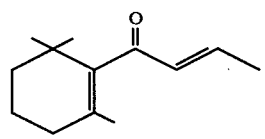

(otherwise known as β-damascone) and compounds having the structures:

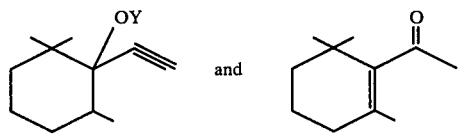

wherein Y is MgX', Li, Na or K and processes for preparing same according to the reaction scheme.

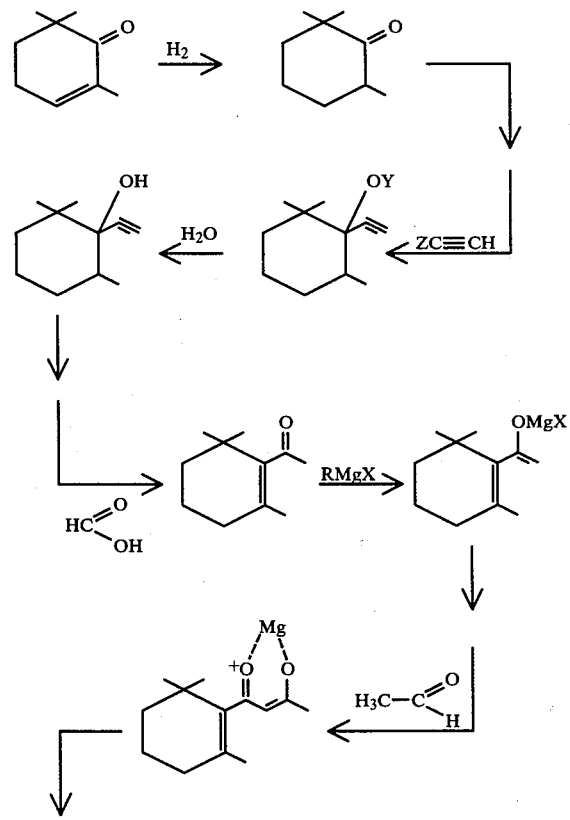

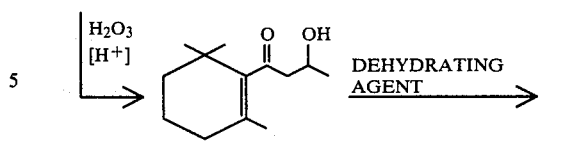

wherein Z is H, MgX', Li, Na or K; Y is MgX', Li, Na or K; X' is Cl, Br or I, R is $C_1$–$C_3$ lower alkyl, such as methyl, ethyl, n-propyl or i-propyl and X is Cl, Br or I. The compound having the structure:

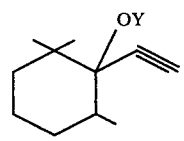

in addition to being newly useful as an intermediate in preparing compounds having the structure:

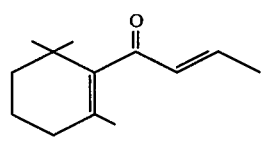

is also useful for its organoleptic properties in augmenting or enhancing the aroma or taste of foodstuffs.

The β-damascone and compounds having the structures:

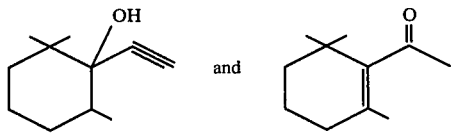

are useful for their organoleptic properties in foodstuffs, foodstuff flavoring compositions, chewing gums, toothpastes, medicinal, medicinal products, perfumes, colognes, perfumed articles and smoking tobaccos.

There is a continuing search for food flavor compositions which can vary, fortify, modify, enhance, augment or otherwise improve the flavor and/or aroma of foodstuffs, medicinal products, toothpastes and chewing gums. To be satisfactory, such compositions should be stable, non-toxic and blendable with other ingredients to provide their own unique flavor and aroma nuances without detracting from the co-ingredients of the formulations in which they are used. Preferably, such compositions should be natural occurring or present in natural foodstuffs so that their ingestible safety can be readily recognized. These materials should be capable of being synthesized in a simple and economical manner. The need for safe flavors in the raspberry, grape, cognac, wine, apple, potato, and red beet area is well known. More specifically, there is a need for the development of non-toxic materials which can replace natural materials not readily available having sweet, rose bud, raspberry-like, concord grape juice-like, wine, apple juice-like, brandy, earthy, geosmin-like, and tropical vegetation-like aromas with sweet, rose bud-like, raspberry-like, concord grape juice-like, wine, brandy-like, earthy, tropical vegetation-like, raw potato-like, geosmin-like and bitter flavor characteristics.

In addition, there has been considerable work performed relating to substances which can be used to impart (modify, augment or enhance) flavors and fragrances to (or in) various other consumable materials, such as smoking tobaccos, perfumes, colognes and perfumed articles, e.g., solid or liquid anionic, cationic or nonionic detergents and drier-added fabric softener articles). Thus, sweet, cooling, earthy, musty, tea, green aroma nuances prior to smoking and tea-hay/fruity, fresh, cooling, citrus peel-like, woody and earthy aroma nuances on smoking in the main stream and in the side stream are desirable in smoking tobaccos and in smoking tobacco flavoring compositions.

Furthermore, earthy, rooty and minty aroma characteristics are desirable in certain types of perfume compositions, perfumed articles and colognes, particularly those having a lavender-like character.

The instant invention provides the foregoing which the prior art has heretofore failed to provide. Furthermore, nothing in the prior art shows the unexpected, unobvious and advantageous value of the compound having the structure:

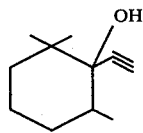

for their organoleptic properties. As is seen above, another of the intermediate compounds produced in the process of our invention has the structure:

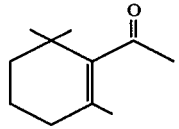

and this compound is disclosed in the prior art at:
  Chem. Abstracts, Vol. 78, No. 110669t (Abstracts of J. Org. Chem. 1973, 38 [5], 894–6);
  Chem. Abstracts, Vol. 80, No. 27395w (Abstracts of J. Chem. Soc., Chem. Communications 1983 [19], 7842; and at
  Chem. Abstracts, Vol. 79, No. 42041a (Abstract of German Offlegungschrift No. 2,244,680). German Offlegungschrift No. 2,244,680 includes a genus which could read on the compound having the structure:

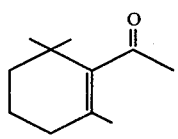

but no specific disclosure thereof is made in said German Offlegungschrift.

In addition, the preparations of these compounds have been carried out in a rather complex manner as is shown in:
  Chem. Abstracts 54:345f (U.S. Pat. No. 2,853,520);
  Chem. Abstracts, Vol. 50, 8540h (Abstract of Chanley, et al, J. Am. Chem. Soc. 77, 6056–7 [1955]);
  Chem. Abstracts 50:15442b (Abstract of Landor, J. Chem. Soc., 1956, 1015–1019);
  Chem. Abstracts, Vol. 48, 13644i (Abstract of Newman, J. Am. Chem. Soc., 75, 4740–2 [1953]); and
  Chem. Abstracts, Vol. 47:1098h (Abstract of Henbest, et al, J. Am. Chem. Soc., 1952, 1150–4)

Nothing in the prior art, however, discloses the use of the compound having the structure:

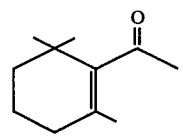

and the compound having the structure:

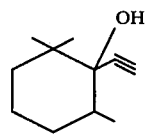

as intermediates for preparing β-damascone having the structure:

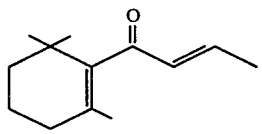

β-Damascone is shown to be useful for its organoleptic properties by Kovatz at Chem. Abstracts, Vol. 74, page 76564k ("Cycloaliphatic Unsaturated Ketones for Use as Perfumes").

Mixtures, presumably predominantly cis, trans-Δ-damascone with minor amounts of trans, trans-Δ-damascone have been produced by Ayyar, Cookson and Kagi as set forth in J. Chem. Soc., Perkin Trans. 1, 1975 (17) 1727–36 [Title: "Sythesis of δ-Damascone[-trans-1-(2,6,6-Trimethylcyclohex-3-enyl)but-2-en-1-one] and β-Damascenone [trans-1-(2,6,6-Trimethyl-cyclohexa-1,3-dienyl)but-2-en-1-one]"]. The reaction sequence of the Ayyar synthesis of compositions presumed to be predominantly cis, trans-Δ-damascone with minor amounts of trans, trans-Δ-damascone is as follows:

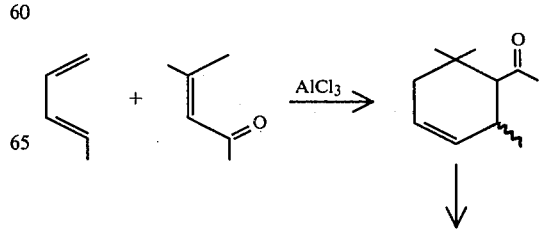

-continued

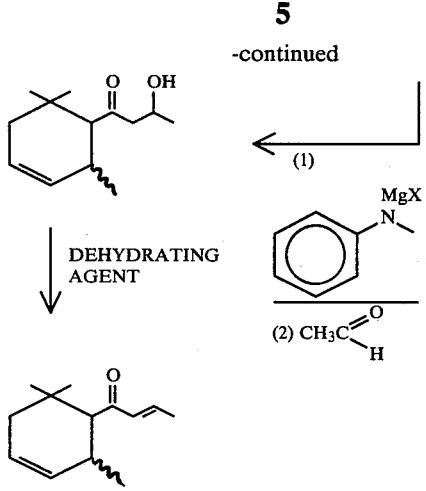

wherein the wavy line is representative of a "cis" or "trans" configuration of the methyl moiety with respect to the acetyl or crotonoyl moiety, both of which are bonded to the cyclohexenyl moiety, the "cis" isomer presumably being the major isomer and the "trans" isomer presumably being the minor isomer in this reaction sequence. In addition, Ayyar, et al also discloses the reaction sequence:

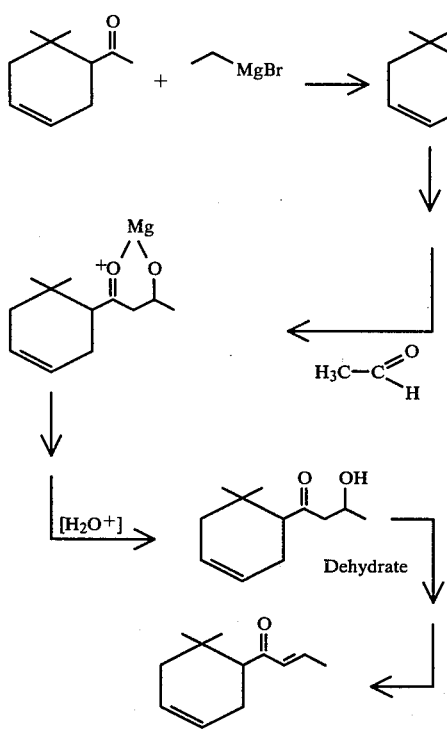

and the use of an acetic hydride dehydrating agent to make the compound having the structure:

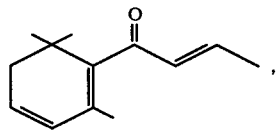

β-damascenone. However, the only procedure for making the compound having the structure:

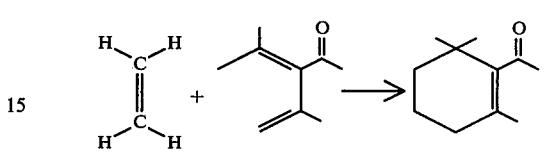

is via a Diels-Alder reaction on page 1728 of Ayyar, et al thus:

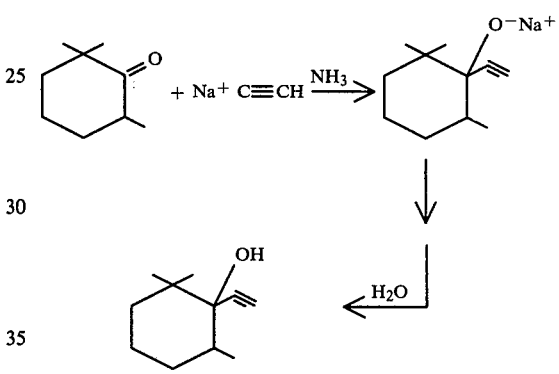

Separate and apart from the Ayyar, et al article is the article by Julia and Tchernoff at Compt. Rend. 249, 714-16 (1959) setting forth the reaction:

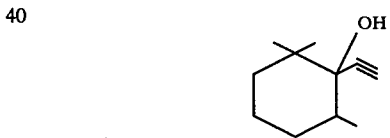

The compound having the structure:

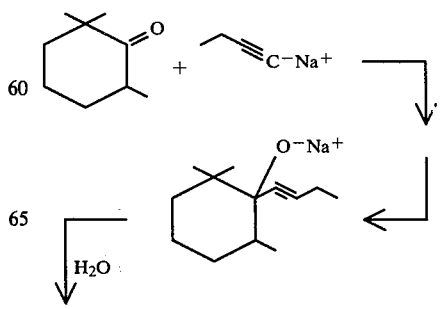

produced according to the foregoing reaction scheme is indicated to the useful in the perfume industry and British Pat. No. 627,453 assigned to the Galaxo Company, Ltd.

Separately from the Julia and Tchernoff article and from the Ayyar, et al article is the article is the article in Agr. Biol. Chem. 37, 2907 (1973) setting forth the reaction scheme for preparing a dihydro form of β-damascone according to the reaction scheme:

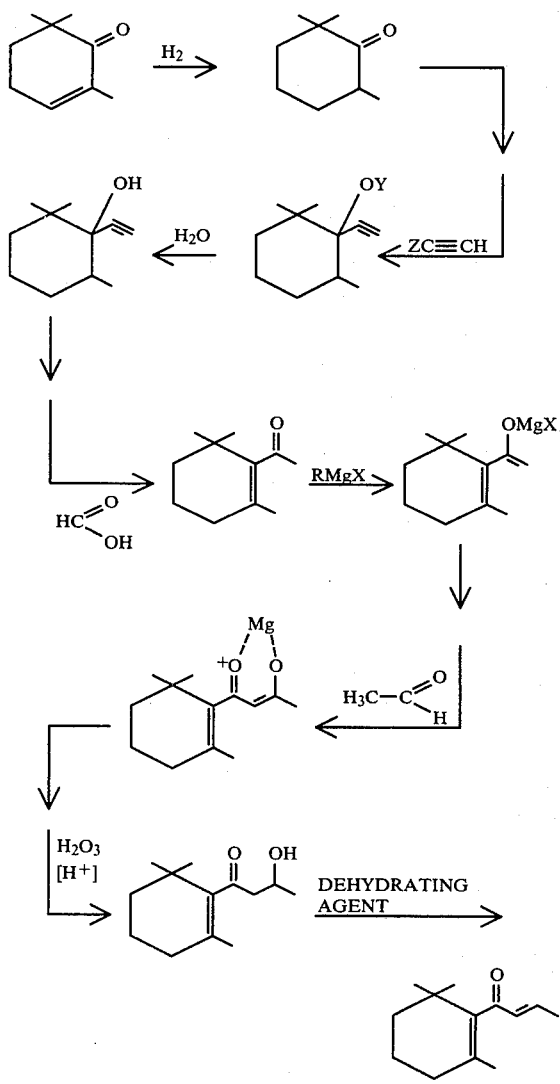

However, the reaction sequence of the instant invention is to prepare β-damascone fails to be taught by any of the prior art either taken alone or together. Nothing in the prior art infers that the various reactions set forth above can be put together to form the one unique reaction sequence:

The use in perfumery of β-damascone having the structure:

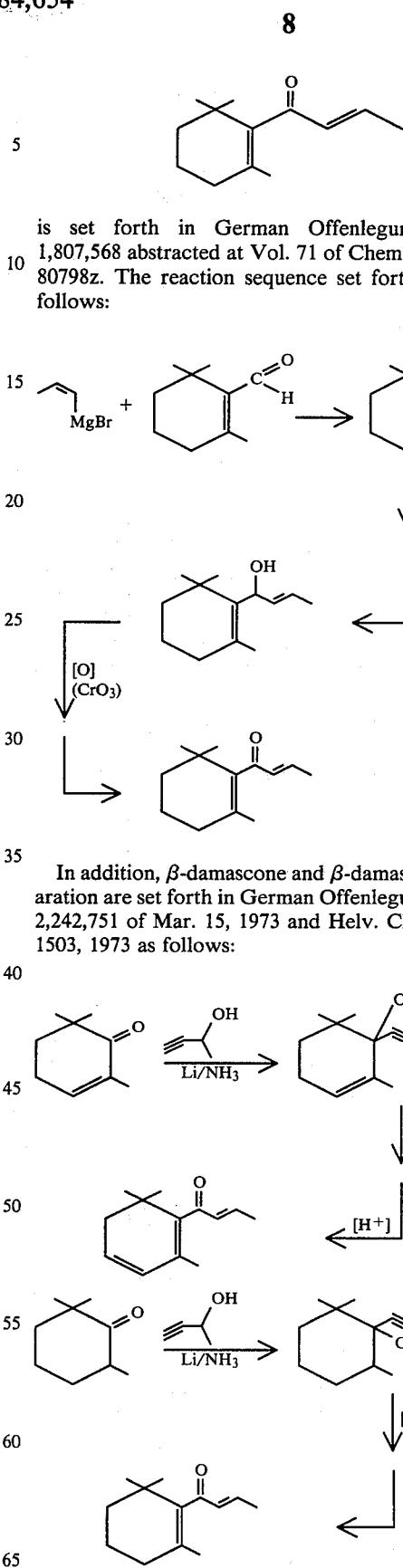

is set forth in German Offenlegungsschrift No. 1,807,568 abstracted at Vol. 71 of Chem. Abstracts No. 80798z. The reaction sequence set forth therein is as follows:

In addition, β-damascone and β-damascenone's preparation are set forth in German Offenlegungsschrift No. 2,242,751 of Mar. 15, 1973 and Helv. Chem. Acta. 56, 1503, 1973 as follows:

Blumenthal in U.S. Pat. No. 2,996,552 issued on Aug. 15, 1961 discloses, broadly, a process for preparing an acetylenic alcohol by the reaction of an aldehyde or a ketone with an acetylenic hydrocarbon in the presence of an alkali metal compound which may be either an alkali metal hydroxide, or an alkali metal alcoholate of a tertiary acetylenic alcohol and discloses that this reaction can be carried out in a reaction medium which is either ethylene diamine or a liquid organic sulfoxide such as dimethyl sulfoxide. Typically, in Example XII of U.S. Pat. No. 2,996,552, it is indicated that acetylene, KOH and acetophenone can be admixed in the presence of ethylene diamine to produce phenyl butynol or in Example VII at column 5, acetylene, KOH and acetophenone can be admixed in the presence of dimethyl sulfoxide to produce 3,5-phenyl-1-butyn-3-ol and 2,5-diphenyl-3-hexyne-2,5-diol.

The immediately aforementioned prior art, however, fails to tie together a sequence of reactions starting with 2,6,6-trimethyl-2-cyclohexenone to form β-damascone and, furthermore, nothing in the prior art discloses the flavor or fragrance utility of the compound having the structure:

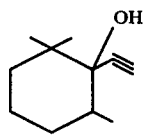

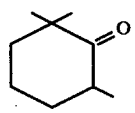

Figure 2:
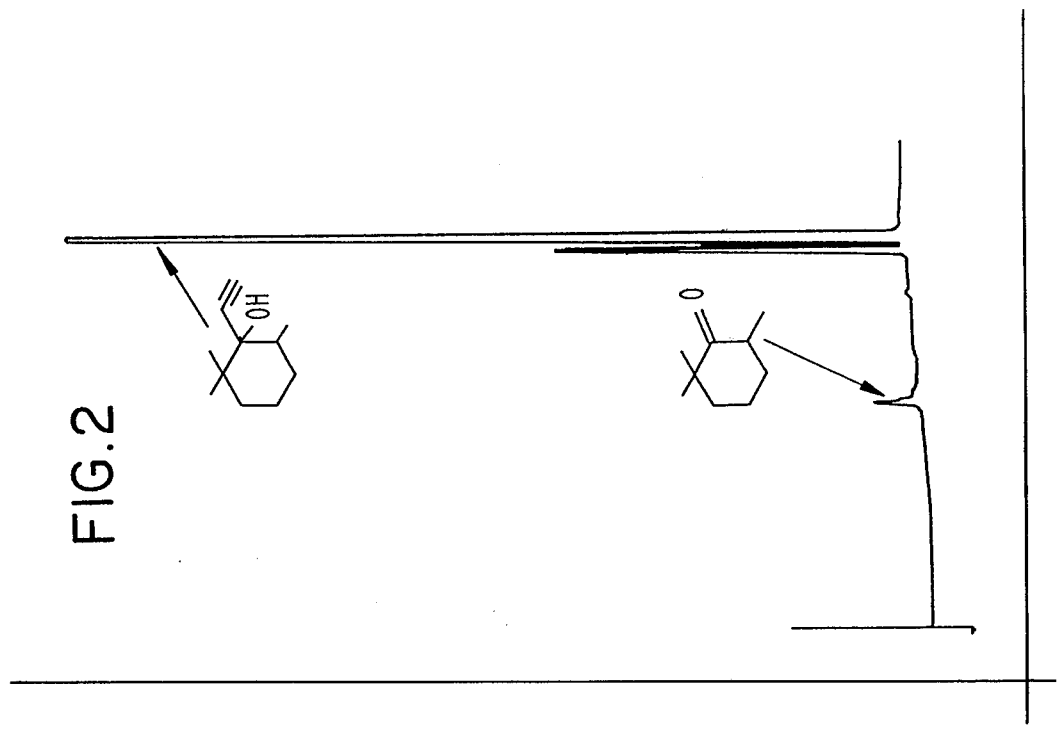
Figure 1:
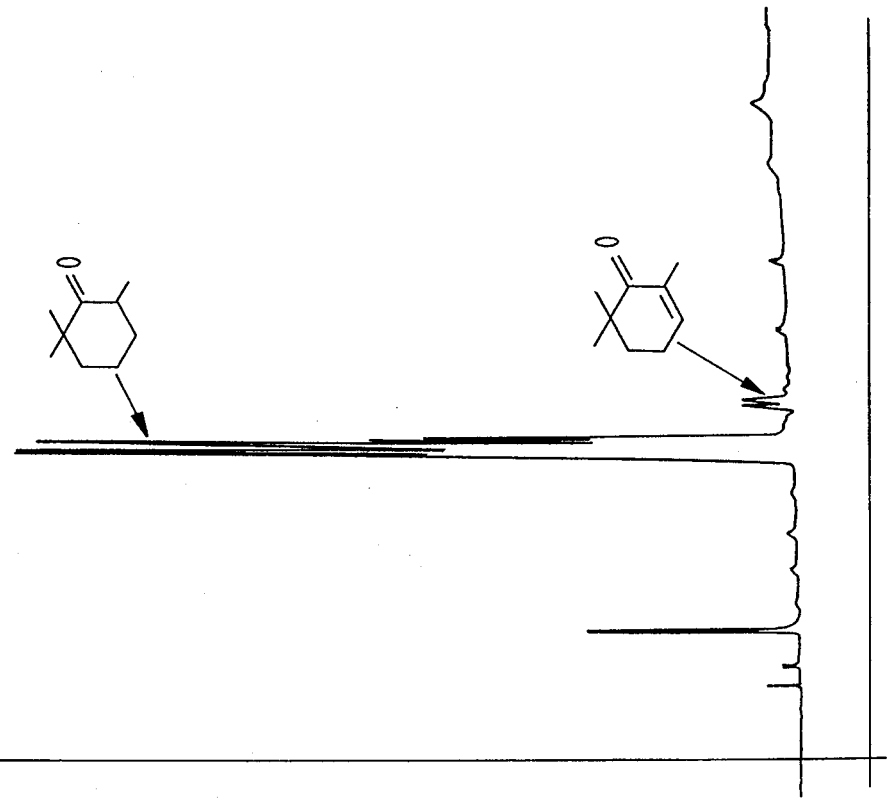
FIG. 1 is the GLC profile of the reaction product produced according to Example I comprising for the most part compound having the structure.

FIG. 2 is the GLC profile of the reaction product produced according to Example II containing for the most part compound having the structure:

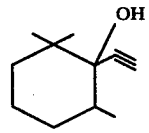

Figure 3:
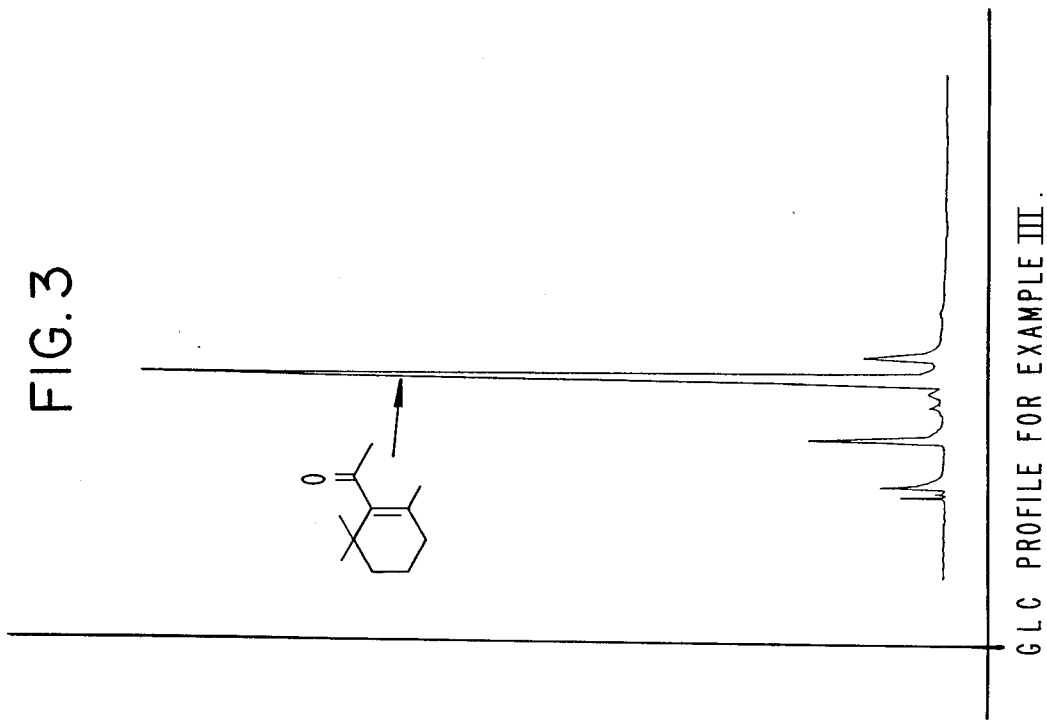

FIG. 3 is the GLC profile of the reaction product of Example III containing for the most part compound having the structure:

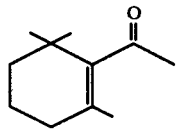

Figure 4:
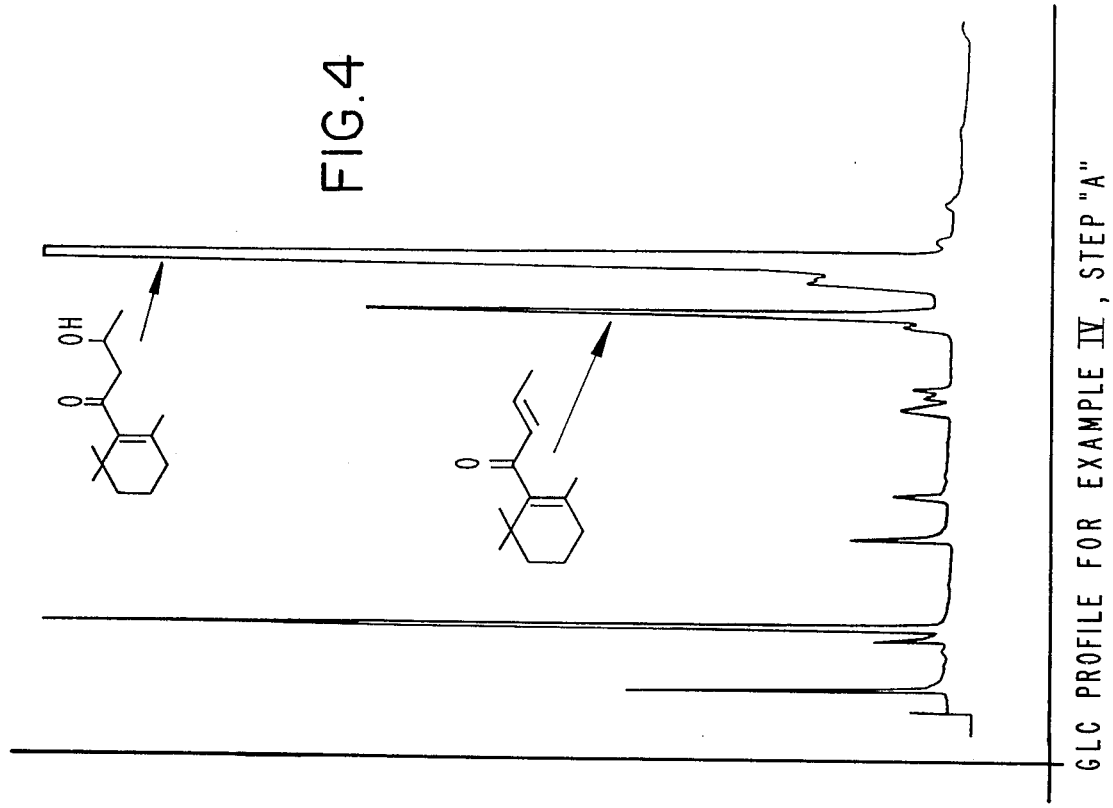

FIG. 4 is the GLC profile of the reaction product produced according to step "A" of Example IV and having for the most part compounds having the structures:

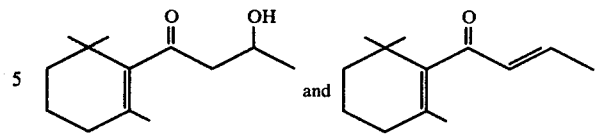

FIG. 5 is the GLC profile of the reaction product produced according to step "B" of Example IV containing for the most part compound having the structure:

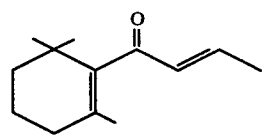

FIG. 6 is the mass spectrum of the compound having the structure:

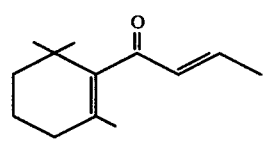

produced according to step "B" of Example IV.

Figure 7:
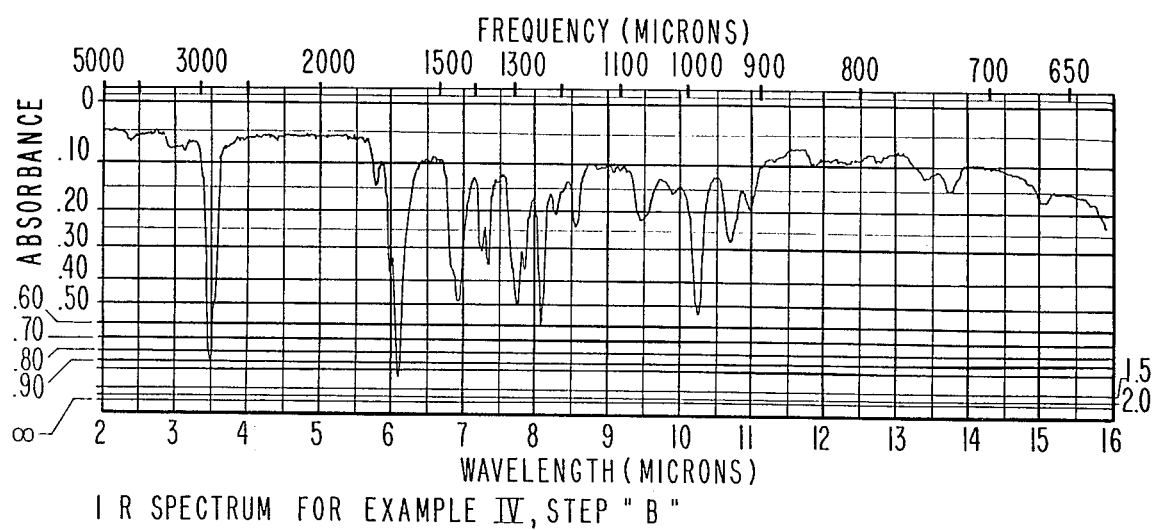

FIG. 7 is the infrared spectrum of the compound having the structure:

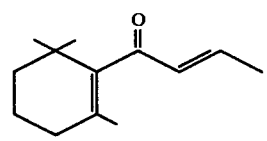

produced according to step "B" of Example IV.

Figure 8:
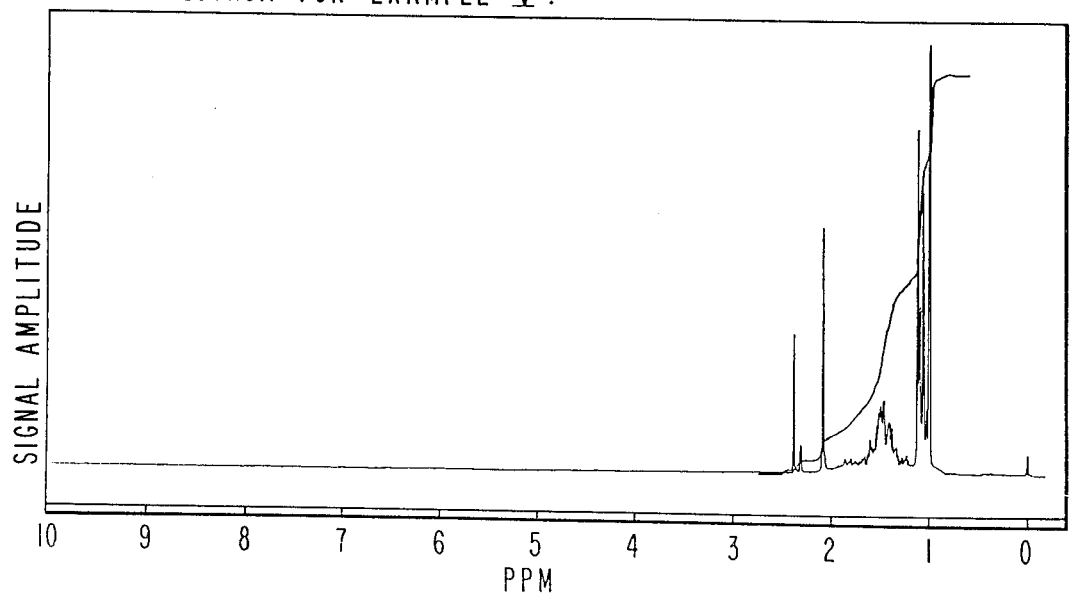

FIG. 8 is the NMR spectrum of the compound having the structure:

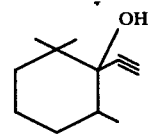

produced according to Example V.

Figure 9:
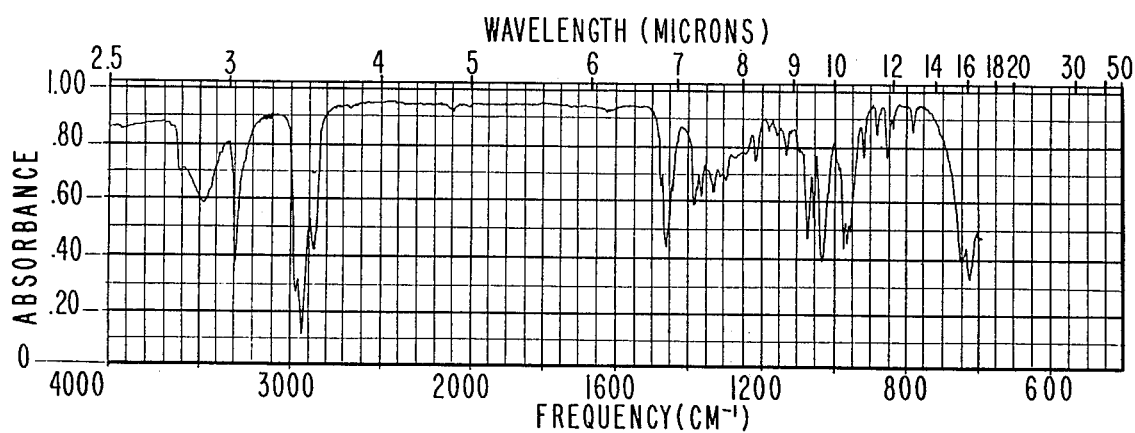

FIG. 9 is the infrared spectrum of the compound having the structure:

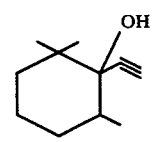

produced according to Example V.

Figure 10:
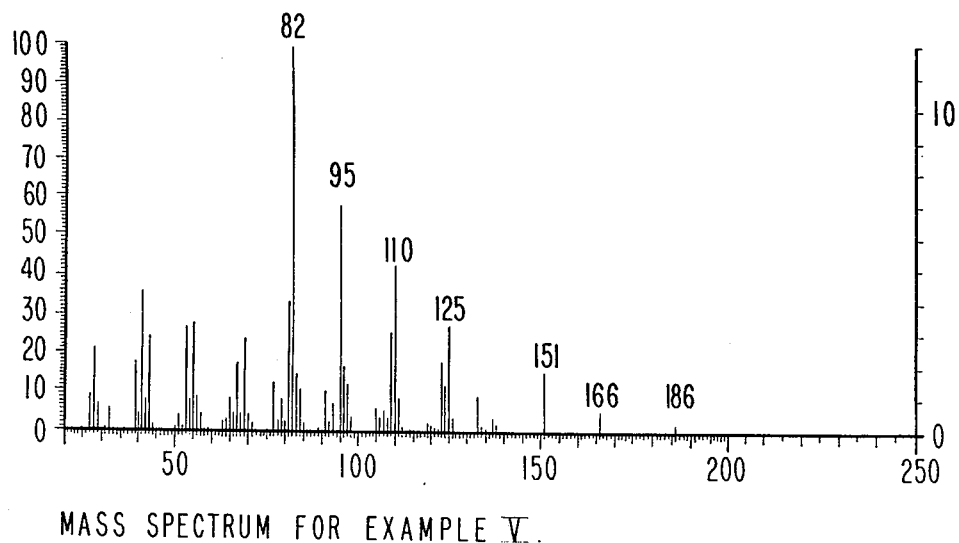

FIG. 10 is the mass spectrum of the compound having the structure:

produced according to Example V.

FIG. 11 is the mass spectrum of the compound having the structure:

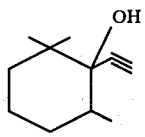

produced according to Example VI.

THE INVENTION

The present invention provides compounds having the structures:

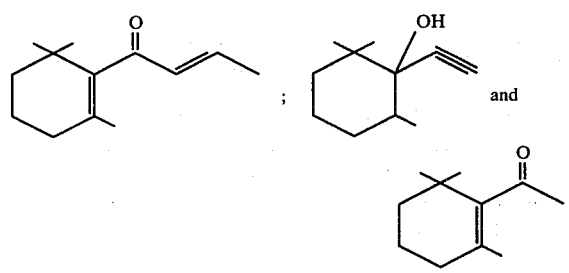

which are useful for their organoleptic properties in augmenting or enhancing the aroma or taste of foodstuffs, chewing gums, medicinal products, toothpastes, perfumes, perfumed articles, such as anionic, cationic and nonionic solid or liquid detergents, colognes, dryer-added fabric softeners, smoking tobaccos, and smoking tobacco articles. Thus, the compounds of the present invention:

(a) Insofar as augmenting or enhancing the aroma or taste of foodstuffs, chewing gums, toothpastes or medicinal products are concerned imparts sweet, rose bud-like, raspberry-like, concord grape juice-like, wine, apple juice-like, brandy-like, earthy, geosmin-like and tropical vegetation-like aromas with sweet, rose bud-like, raspberry-like, concord grape-like, wine, brandy-like, earthy, tropical vegetation-like, raw potato-like, geosmin-like and bitter flavor characteristics useful for raspberry, grape, cognac, wine, apple, potato and red beet flavors;

(b) In perfumes, the earthy, rooty, musty, borneol-like, minty and camphoraceous aromas are augmented or enhanced;

(c) In smoking tobaccos and smoking tobacco articles, sweet, cooling, pungent, camphoraceous, woody and earthy aroma nuances are augmented or enhanced prior to or on smoking.

The present invention also provides processes for preparing such compounds and intermediates. Such a process is summarized and illustrated by the reaction sequence:

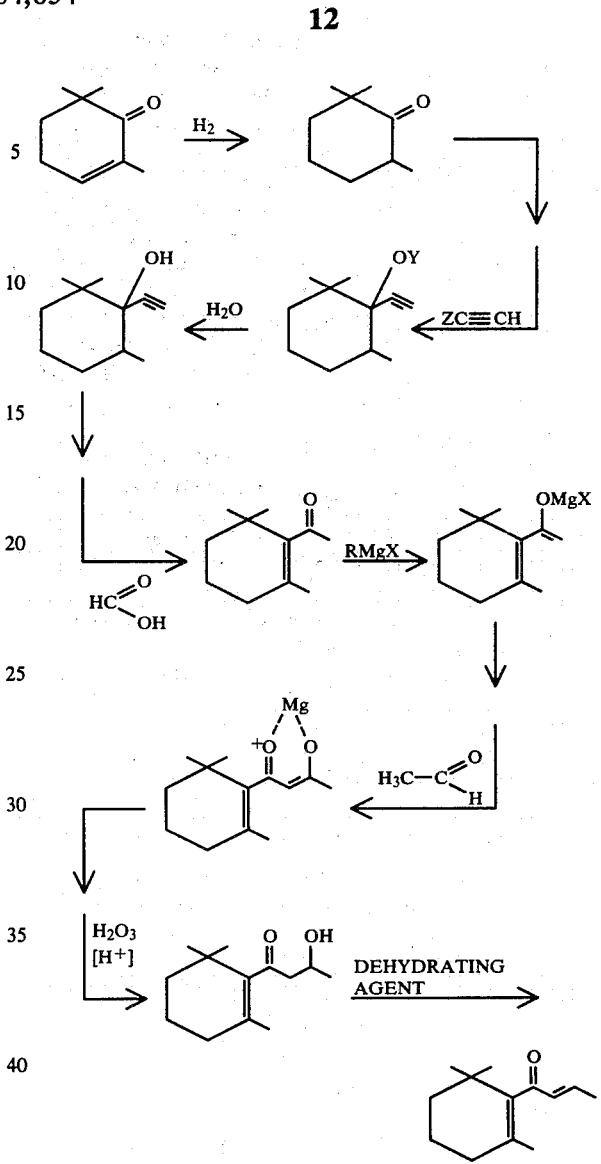

The process of our invention first includes the step of carrying out a hydrogenation reaction by reacting the compound having the structure:

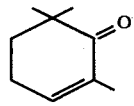

with hydrogen over a catalyst such as a Lindlar catalyst (palladium suspended on calcium carbonate) or a palladium on carbon catalyst (e.g., 5% palladium on carbon; 7% palladium on carbon; 10% palladium on carbon or 15% palladium on carbon) thus forming a compound having the structure:

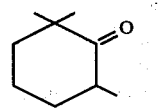

The resulting compound is then reacted further with an alkali metal acetylide, such as sodium acetylide thereby forming the compound having the structure:

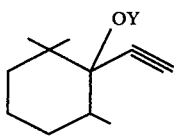

wherein Y is alkali metal. The reaction conditions used for carrying out this reaction are similar to those set forth in the paper by Mori Agricultural and Biological Chemistry, Vol. 37, No. 12, December, 1973 at pages 2908, 2909 and 2910 or under the conditions of the Blumenthal U.S. Pat. No. 2,996,552 issued on Aug. 15, 1961 using instead of an alkali metal acetylide, an alkali metal hydroxide, acetylene and the compound having the structure:

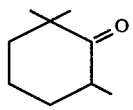

and either ethylene diamine or an alkali metal sulfoxide, such as dimethyl sulfoxide. Preferably, the reaction involving the alkali metal acetylide and compound having the structure:

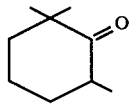

takes place at temperatures of between −50° C. and −10° C. at atmospheric pressure. When using ethylene diamine or dimethyl sulfoxide, the alkali metal hydroxide employed is preferably of about 90% or higher purity and finally divided, i.e., 80–100 mesh or higher. The optimum loading per liter of liquid organic sulfoxide or ethylene diamine is from about 0.38 up to about 0.5 moles of alkali metal hydroxide or alcoholate and 5.0 to 6.25 moles of compound having the structure:

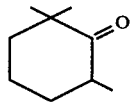

The reaction temperature employed may vary from about −10° C. up to about +80° C. Preferably, the reaction temperature is from about 0° C. up to about 40° C. Pressure does not appear to be a parameter in this reaction and the reaction therefore is preferably conducted at atmospheric pressure although elevated pressures may be used to obtain slight improvements in conversions.

The alkali metal salt having the structure:

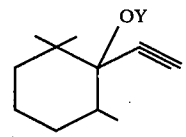

is converted into the tertiary alcohol by hydrolysis using weak acid, such as dilute hydrochloric acid to yield the compound having the structure:

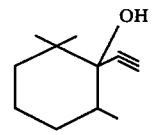

This compound is then reacted with formic acid according to the reaction:

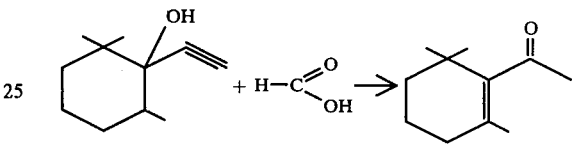

under conditions set forth substantially according to the paper by Mori, et al at Agricultural and Biological Chemistry, Vol. 37, No. 12, December, 1973, pages 2907–2910. Thus, the compound having the structure:

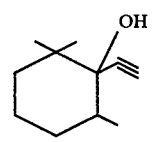

is dissolved in formic acid and the resulting mixture is heated to reflux for a period of between 30 minutes and two hours at atmospheric pressure. The resulting mixture is then diluted with water and extracted with ether and the ether extract is neutralized using weak base, such as sodium bicarbonate and dried and concentrated. The resulting concentrate is then fractionally distilled to yield substantially pure compound having the structure:

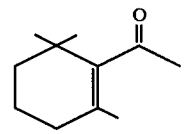

The resulting material having the structure:

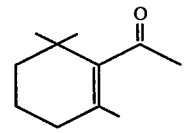

can be used as is for its organoleptic properties particularly in the foodstuff flavor and the tobacco flavor area.

The resulting compound is then reacted with an alkyl grignard reagent such as ethyl magnesium chloride to form a first organometallic compound having the structure:

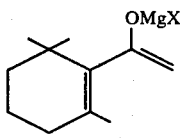

This first organometallic compound (wherein X is chloro, bromo or iodo) is reacted with acetaldehyde to form a second organometallic compound having the structure:

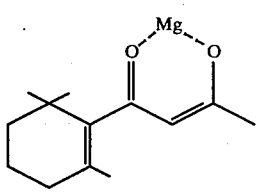

This second organometallic compound is hydrolyzed in weak acid to form a hydroxy ketone having the structure:

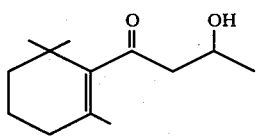

which may be used for its organoleptic properties in foodstuff flavors, perfumes, perfumed articles, or tobacco flavors or which may be dehydrated with a dehydrating agent, such as acetic anhydride. The over-all reaction sequence is as follows:

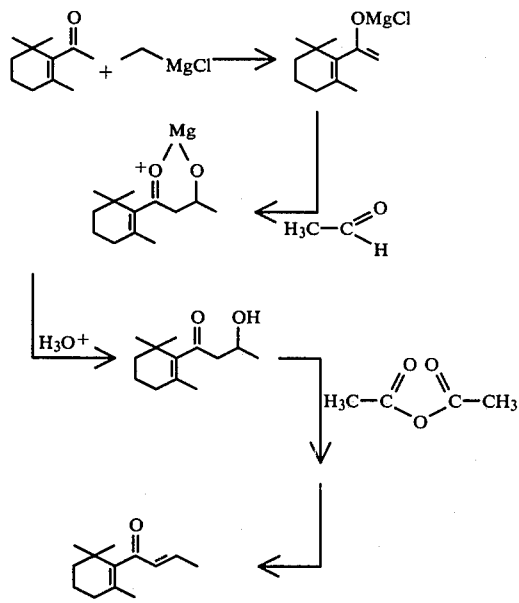

The resulting β-damascone may be purified as by fractional distillation.

The reaction of the 2,6,6-trimethyl-1-acetylcyclohexene with the alkyl Grignard is carried out with the Grignard reagent having the structure RMgX where R is $C_1$–$C_6$ alkyl and wherein X is halogen selected from the group consisting of chloro, bromo and iodo. This reaction of the lower alkyl Grignard reagent with the 2,6,6-trimethyl-1-acetylcyclohexene derivative is carried out in the presence of a solvent which is inert in the reaction mass, for example, diethyl ether or tetrahydrofuran. The reaction temperature is preferably between 20° and 35° C. at atmospheric pressure. Higher pressures or lower pressures and higher temperatures or lower temperatures may be used but there is no advantage in so using the temperature outside of the range of 20°–35° C. and pressures outside of one atmospheres (ambient conditions).

After the compound having the structure:

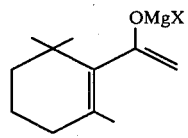

is formed, the resulting material is reacted with acetaldehyde and then water to form a hydroxy ketone having the structure:

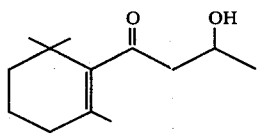

The reaction temperature for this reaction is preferably between −10° C. and +15° C.; more preferably, between 0° C. and 10° C. at atmospheric pressure. The acetaldehyde is added to the compound having the structure:

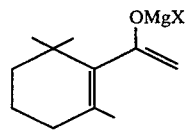

in admixture with an inert solvent, such as toluene or xylene. It is preferred that the weight ratio of inert solvent, such as toluene or xylene:acetaldehyde be in the range of from about 2:1 up to about 5:1 with a preferred weight ratio of solvent, such as toluene or xylene:acetaldehyde being about 3–4:1. At the completion of the reaction of the compound having the structure:

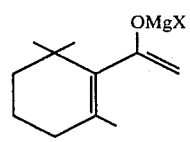

with acetaldehyde, the resulting reaction product is then admixed with water at a temperature of between 10° C. and 40° C., preferably, between 15° C. and 25° C. at one atmosphere pressure. The resulting compound, the hydroxy ketone having the structure:

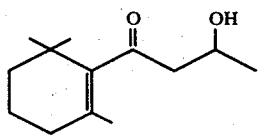

may be separated as by fractional distillation and may be used for its organoleptic properties or it may be further dehydrated with a dehydrating agent, such as acetic anhydride whereby β-damascone having the structure:

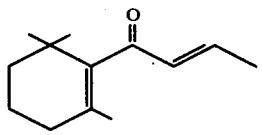

is formed. The dehydration reaction takes place in the presence of an inert solvent, such as toluene or xylene and the dehydration reagent is a compound such as acetic anhydride, phosphoric acid or para toluene sulfonic acid. The dehydration also takes place in the presence of a weak base, such as sodium acetate, potassium acetate, sodium carbonate or potassium carbonate. The weight ratio of keto alcohol:solvent may vary from 1:0.5 (keto alcohol:solvent/weight:weight) up to 1:10 with a preferred ratio of between 1:0.5 and 1:1. The mole ratio of keto alcohol:dehydrating agent is preferably between 1:0.25 and 1:1 (keto-alcohol:dehydrating agent) and the weight ratio of dehydrating agent:weak base is preferably between 1:1 and 10:1 with a weight ratio of from 4:1 up to 5:1 of dehydrating agent:weak base being preferred. The resulting β-damascone is then fractionally distilled in order to make it suitable for use in augmenting or enhancing the aroma or taste of consumable materials, such as smoking tobaccos, foodstuffs, perfumes, perfumed articles and colognes.

The term "substituted cyclohexane derivative" is hereinafter intended to mean compounds having the structures:

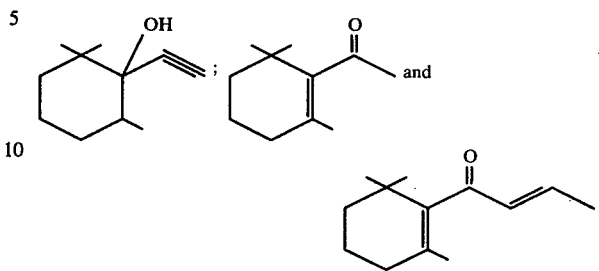

Specific examples of the compounds produced according to the foregoing processes are set forth in Table I below:

TABLE I

| STRUCTURE OF COMPOUND | NAME OF COMPOUND | PERFUMERY EVALUATION | FLAVOR EVALUATION | TOBACCO EVALUATION |
|---|---|---|---|---|
|  | 1-ethynyl-2,2,6-trimethylcyclohexen-1-ol | A strong, minty, camphoraceous, borneol-like note with an earthy beet root character. | A sweet, earthy, tropical vegetation, geosmin-like aroma with a sweet, earthy, tropical vegetation-like, geosmin-like, potato, bitter flavor characteristic at 0.05 ppm. | An earthy, sweet, floral, citrus aroma prior to and on smoking in the main stream and in the side stream. |
|  | 1-acetyl-2,2,6-trimethylcyclohexen-1 | An earthy, rooty, musty, borneol-like aroma. | An earthy, greenhouse-like, floral aroma with an earthy greenhouse-like floral bitter flavor. | Prior to smoking, a sweet, cooling, pungent, camphoraceous, earthy aroma and taste and on smoking, a fresh, slightly cooling, citrus peel-like, woody, cooling, earthy aroma in the main stream and in the side stream. |
|  | beta-damascone | A rose-floral, fruity, prune, berry aroma. | A floral, rosebud, woody, fruity, ripe raspberry, raisin, grape juice-like aroma and taste. | A sweet, fruity, hay-like, minty, spicy, woody aroma prior to smoking and a sweet, fruity aroma and taste on smoking in the mainstream and in the sidestream. |

When the substituted cyclohexane derivatives of our invention are used as food flavor adjuvants, the nature of the co-ingredients included with each of the said substituted cyclohexane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates one or more of the substituted cyclohexane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, tumeric and curcuma and the like, firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpineol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetone, dimethyl sulfide, alpha-ionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexene-1-ol, 2-hexenyl acetate, 2-hexenyl butyrate, hexyl butyrate, 4-(p-hydroxyphenyl)-2-butanone, beta-ionone, isobutyl cinnamate, jasmine, lemon essential oil, methyl butyrate, methyl caproate, methyl disulfide, methyl-p-naphthyl ketone, orris butter, rose absolute, terpenyl acetate, gammaundecalactone, vanilla and alcohol.

The specific flavoring adjuvant selected for use may be either solid or liquid depending upon the desired physical form of the ultimate product, i.e., foodstuff, whether simulated or natural, and should, in any event, (i) be organoleptically compatible with the substituted cyclohexane derivatives of our invention by not covering or spoiling the organoleptic properties (aroma and/or taste) thereof; (ii) be nonreactive with the substituted cyclohexane derivatives of our invention and (iii) be capable of providing an environment in which the substituted cyclohexane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of substituted cyclohexane derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum, per se, medicinal product per se, toothpaste per se, of flavoring composition.

The use of insufficient quantities of substituted cyclohexane derivatives will, of course, substantially vitiate any possibility of obtaining the desired results while excess quantities prove needlessly costly and, in extreme cases, may disrupt the flavor-aroma balance, thus providing self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of substituted cyclohexane derivatives ranging from a small but effective amount, e.g., 0.02 parts per million up to about 500 parts per million based on total composition are suitable. Concentrations in excess of the maximum quantity stated are not normally recommended, since they fail to prove commensurate enhancement of organoleptic properties. In those instances, wherein the substituted cyclohexane derivatives are added to the foodstuff as an integral component of a flavoring composition, it is, of course, essential that the total quantity of flavoring composition employed be sufficient to yield an effective substituted cyclohexane derivative concentration in the foodstuff product.

Food flavoring compositions prepared in accordance with the present invention preferably contain the substituted cyclohexane derivatives in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the substituted cyclohexane derivatives with, for example, gum arabic, gum tragacanth, carrageenan and the like, and thereafter spray-drying the resultant mixture whereby to obtain the particular solid product. Pre-prepared flavor mixes in powder form, e.g., a fruitflavored powder mix are obtained by mixing the dried solid components, e.g., starch, sugar and the like and substituted cyclohexane derivatives in a dry blender until the requisite degree of uniformity is achieved.

It is presently preferred to combine with the substituted cyclohexane derivatives of our invention, the following adjuvants:

2,3-Diethyl pyrazine;
Methional;
Furfural;
Dimethylsulfide;
Isovaleraldehyde;
Diacetyl;
2,4-Decadienal;
Phenylacetaldehyde;
Hexanal;
Tetrahydro Quinoxaline;
Vanillin;
Maltol;
Parahydroxy phenyl butenone;
Alpha ionone;
Ethyl butyrate;
Isobutyl acetate;
Ethyl acetate;
Acetic acid; and
Acetaldehyde The following examples serve to illustrate the processes for specifically producing the substituted cyclohexane derivatives of our invention and also serve to illustrate specific embodiments of our invention. It will be understood that these examples are illustrative and the invention is to be considered restricted thereto only as indicated in the appended claims.

All parts and percentages given herein are by weight unless otherwise specified.

EXAMPLE I

REDUCTION OF 2,6,6-TRIMETHYL-2-CYCLOHEXENONE

Reaction:

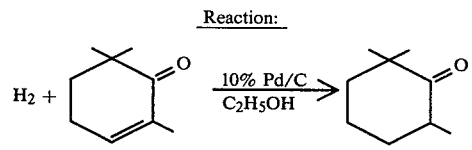

10.0 Grams of 2,6,6-trimethyl-2-cyclohexenone, 40 ml of anhydrous ethanol and 0.5 grams of 10% palladium-on-carbon are charged into a Parr pressure shaker flask. The apparatus is purged several times with hydrogen. Reduction is carried out over a period of 1.5 hours at 50 psig hydrogen pressure. Infrared analysis confirms the formation of 2,6,6-trimethyl-2-cyclohexanone (40 grams).

EXAMPLE II

PREPARATION OF 1-ETHYNYL-2,2,6-TRIMETHYL CYCLOHEXAN-1-OL

Reaction:

Na + NH$_3$ →NaNH$_2$

NaNH$_2$ + HC≡CH →HC≡C$^-$Na$^+$

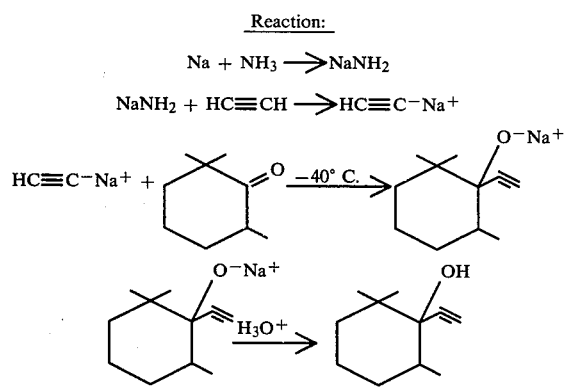

Into a two liter reaction flask equipped with mechanical stir, two glass "Y"'s, a thermometer, an addition funnel, a condenser, a thermometer, an adapter with glass tube for addition of ammonia and acetylene, and a dry ice bath is placed a suspension of NaNH$_2$ prepared from 8 grams of Na and 1 liter of liquid ammonia. The suspension is formed by charging ammonia and sodium into the reaction flask.

About 10 grams of acetylene are added over a 30 minute period to the stirred suspension while maintaining the temperature at −50° C. Stirring is continued for a period of 3 hours at −40° C. 2,6,6-Trimethyl-2-cyclohexanone (40 grams) is added to the stirred mixture while maintaining the temperature at −40° C. over a 30 minute period. The stirring is continued for a period of 2 hours. The resulting mixture then remains at room temperature for a period of about 15 hours in order to remove the excess ammonia.

50 Ml water is then added to the reaction mass destroying the remaining unreacted sodium.

The resulting reaction mass is acetified with dilute sulfuric acid and extracted with diethyl ether. The diethyl ether extract is dried over anhydrous magnesium sulfate and concentrated. The reaction flask contents are then transferred to a separatory funnel and acetified with three 100 ml 5% sulfuric acid volumes. The resulting water layer is extracted with three 100 ml diethyl ether volumes. The diethyl ether extracts are combined and washed with three 50 ml portions of saturated sodium chloride. The resulting ether extracts are then dried over anhydrous magnesium sulfate and evaporated on a rotary evaporator yielding 43.4 grams of product. Fraction 6 of the resulting distillation product has a sweet, earthy, tropical vegetation-like, geosmin-like aroma and a sweet, earthy, tropical, vegetation-like, potato, geosmin-like and bitter flavor making it useful for potato and red beet flavors at a concentration of 0.05 ppm. It also has earthy, sweet, floral and citrusy notes prior to and on smoking in the main stream and in the side stream when tested in a smoking tobacco. It also has a strong minty, camphor, borneol note with an earthy, beet root characteristic when tested as a perfume material.

EXAMPLE III

PREPARATION OF 1-ACETYL-2,6,6-TRIMETHYL-CYCLOHEXA-1-ENE

Reaction:

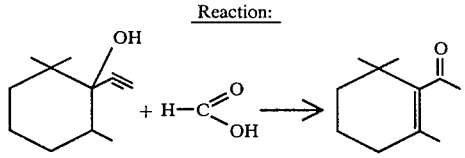

Into a 250 ml micro reaction flask equipped with magnetic stir, condenser, thermometer and heating mantle is placed a solution of 43.3 grams of compound having the structure:

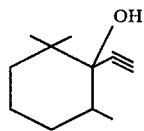

produced according to Example II dissolved in 90% formic acid (100 ml). The resulting mixture is heated under reflux for a period of one hour. The mixture is then diluted with water and extracted with diethyl ether. The diethyl ether extract is washed with water, sodium bicarbonate solution and salt solution and dried over anhydrous magnesium sulfate and concentrated. Thus, the reaction mass is diluted with 100 cc's water and the aqueous and organic layers separated. The aqueous layer is extracted with three 50 ml diethyl ether volumes. The organic layers are combined and washed with three 30 ml volumes of water and then washed with three 50 ml volumes of sodium bicarbonate. Finally, the organic layer is washed with three 50 ml volumes of saturated sodium chloride and dried over anhydrous magnesium sulfate yielding 34.9 grams of crude material. The crude material is then rushed over a micro rushover column at a vacuum of 1.8 mm Hg. and a vapor temperature of 45° C. The resulting material as confirmed by NMR, IR and mass spectral analyses is 1-acetyl-2,6,6-trimethyl-cyclohexa-1-ene having the structure:

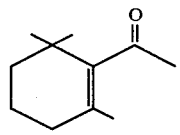

EXAMPLE IV

PREPARATION OF β-DAMASCONE

Reaction:

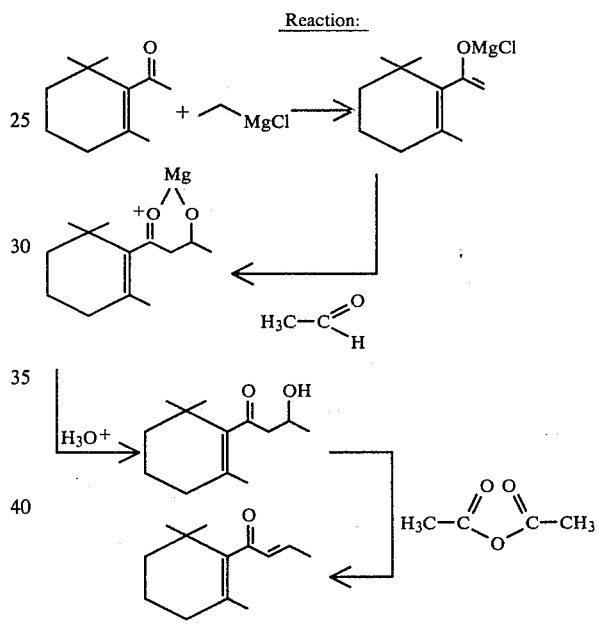

STEP "A"

460 Ml of a solution of ethyl magnesium chloride in 100 ml of toluene is charged into a three liter reaction flask equipped with mechanical stir, thermometer, addition funnel, heating mantle, reflux condenser and water cooler. The reaction mass is heated to 30°–35° C. and over a one hour period, 146.6 grams of 1-acetyl-2,6,6-trimethyl-cyclohex-1-ene having the structure:

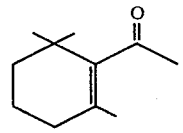

is added. The reaction mass is then stirred for an additional 30 minutes at 25°–35° C. The reaction mass is then cooled to 0° C. and the acetaldehyde (67.5 grams dissolved in 337 ml dry toluene) is added over a one hour period while maintaining the temperature of the reaction mass at 0° C.-10° C. The reaction mass is then stirred for an additional half hour at 0° C.-10° C. Water is then added to the reaction mass and cooling is applied to maintain the temperature at 15°-25° C. The addition will cause some formation of solids on the sides of the flask. Stirring is continued for a period of one hour.

The reaction mixture is then transferred to a separatory funnel and 250 ml water is added along with 500 ml diethyl ether. 300 Ml 2% sulfuric acid is then added to the mixture to break the emulsion that is formed.

The organic and aqueous layers are separated and the aqueous layer is extracted with three 500 ml volumes of diethyl ether. The organic layers are combined and washed with three 750 ml volumes of sodium chloride solution. The resulting product is dried once over a anhydrous magnesium sulfate and most solvent is evaporated off using a rotary evaporator. The weight of the crude material is 204.9 grams. IR, NMR and mass spectral analyses confirm that the resulting product has the structure:

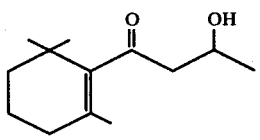

FIG. 4 sets forth the GLC profile for the reaction product.

STEP "B"

Into a two liter reaction flask equipped with magnetic stir, thermometer, addition funnel, reflux condenser and heating mantle is added 18.0 grams of sodium acetate and 80.0 grams of acetic anhydride. The resulting mixture is heated to 105° C. and the compound having the structure:

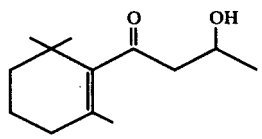

(204.9 grams dissolved in 250 ml toluene) is added over an one hour period to the reaction mass maintaining a temperature of 105°-110° C.

After addition of the keto alcohol, the resulting mixture is heated at 110° C. for an additional 30 minutes. The reaction is monitored by gas chromatography. The reaction mixture is cooled to 75° C. and about 500 grams of water are added. Cooling is required during the water addition.

The water layer is separated and discarded and the organic layer is washed with 10% sodium chloride solution and water thusly. The reaction mass is transferred to a two liter separatory funnel and the flask is rinsed with diethyl ether and the water layer is separated and set aside. The organic layer is then washed with three 250 ml volumes of 10% sodium chloride and three 250 ml volumes of water. The organic layer is dried over anhydrous magnesium sulfate and filtered by gravity. The resulting solvent is evaporated off on a rotary evaporator yielding 225 grams of product. This material is then rushed over on a rush over column and NMR, IR and mass spectral analyses yield the information that the resulting compound is β-damascone having the structure:

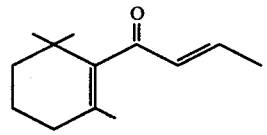

FIG. 5 is the GLC profile for the reaction mass prior to distillation. FIG. 6 is the mass spectrum and FIG. 7 is the infrared spectrum of β-damascone having the structure:

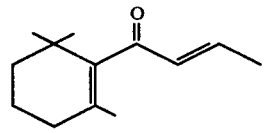

EXAMPLE V

PREPARATION of 1-ETHYNYL-2,2,6-TRIMETHYL-CYCLOHEXANOL

Reaction:

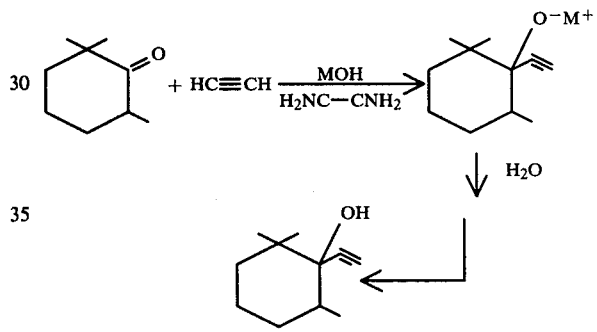

wherein M is potassium.

Into a one liter reaction flask under acetylene is charged 370 grams of ethylene diamine. 7.9 Grams of crushed solid potassium hydroxide is then added to the ethylene diamine with stirring. The acetylene is then fed into the reaction mass over a period of 15 minutes while bubbling at a very slow rate. While maintaining the reaction mass at 25° C., 2,6,6-trimethyl-cyclohexanone prepared according to Example I (140 grams) is added over a period of one hour while maintaining the reaction temperature at between 18° and 24° C.

10 Grams of dry ice (solid carbon dioxide) is added to the reaction mass and the reaction mass color turns from pink to light green. The reaction mass is then transferred to a three liter separatory funnel and one liter of water is added thereto. 250 Ml toluene are then added thereto. The aqueous and organic phases are separated. The organic phase is washed with 300 ml 20% acetic acid; 250 ml saturated sodium bicarbonate; 250 ml saturated sodium chloride.

The reaction mass is concentrated and then distilled on a rush-over column yielding the following fractions:

| Fraction No. | Vapor Temp. | Liquid Temp. | Vac. mm. | Weight of Fraction |
|---|---|---|---|---|
| 1 | 45/63 | 71/74 | 150/155 | 41.5 |

| Fraction No. | Vapor Temp. | Liquid Temp. | Vac. mm. | Weight of Fraction |
|---|---|---|---|---|
| 2 | 60 | 72 | 130 | 45.3 |
| 3 | 53 | 68 | 90 | 42.3 |
| 4 | 47 | 65 | 35 | 45.4 |
| 5 | 33 | 81 | 3 | 5.1 |
| 6 | 84 | 87 | 5 | 42.3 |
| 7 | 83 | 87 | 5 | 46.8 |
| 8 | 67 | 98 | 3 | 41.6 |
| 9 | 58 | 188 | 3 | 3.3 |

The yield is 82% of theory. The resulting product has the structure:

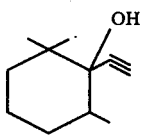

as confirmed by NMR, IR and mass spectral analyses.

FIG. 8 is the NMR analysis for the compound having the structure:

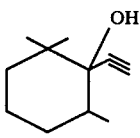

FIG. 9 is the infrared analysis of the compound having the structure:

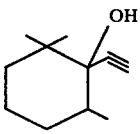

FIG. 10 is the mass spectral analysis for the compound having the structure:

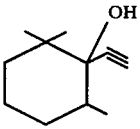

EXAMPLE VI

PREPARATION OF 1-ETHYNYL-2,2,6-TRIMETHYL-CYCLOHEX-ANOL-1 (SCALE-UP)

Reaction:

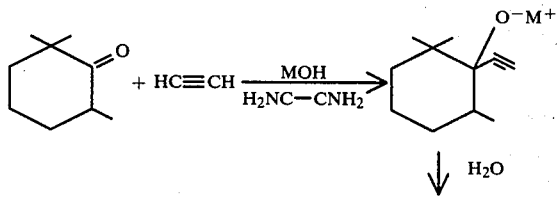

↓ H₂O

-continued
Reaction:

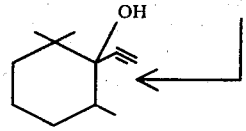

wherein M is potassium.

Into a three liter reaction flask under acetylene gas is added 750 grams of ethylene diamine and 20 grams of crushed potassium hydroxide. The reaction mass is saturated with acetylene using a "Primol ®bubbler". 350 Grams of 2,6,6-trimethyl-cyclohexanone is added to the reaction mass over a period of one hour while maintaining the temperature thereof between 18° and 23° C. The reaction mass is quenched with water and 150 grams of dry ice is then added slowly to the reaction mass. The reaction mass is stirred for a period of 15 hours and then filtered. After filtering, the organic layer weighs 1113.6 grams. Solvent is then stripped and the reaction mass is washed twice with water to a pH of 12 and once with 8% acetic acid to a pH of 4 and once more with water and then twice with saturated sodium chloride solution. The volume of each of the washes is one liter.

The reaction mass is then distilled in a distillation column at 60° C. vapor temperature; 102° C. liquid temperature; 150 mm Hg vacuum.

FIG. 11 is the mass spectrum for the product having the structure:

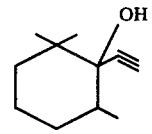

EXAMPLE VII

USE OF 1-ETHYNYL-2,2,6-TRIMETHYL-CYCLOHEX-ANOL IN BASIC BAKED POTATO FORMULATION

The following basic baked potato formulation is prepared.

| Ingredients | Parts by Weight |
|---|---|
| 2,3-Diethyl pyrazine | 4.0 |
| Methional (10% solution in food grade ethanol) | 5.0 |
| Furfural | 0.5 |
| Dimethyl sulfide | 2.0 |
| Isovaleraldehyde | 0.5 |
| Diacetyl (10% in food grade ethyl alcohol) | 1.0 |
| 2,4-decadienal 10% in food grade ethanol) | 0.5 |
| Phenyl acetaldehyde (1% in food grade ethanol) | 0.5 |
| Hexanal (10% in food grade ethanol) | 1.0 |
| Tetrahydro Quinoxaline (1% in food grade ethanol) | 5.0 |
| Ethyl alcohol, food grade 95% | 80.0 |
| 1,2-Propylene glycol | 900.0 |

The basic baked potato formulation is compared at the rate of 10 ppm in water with and without the addition of 1-ethynyl-2,2,6-trimethyl-cyclohexanol prepared according to each of Examples II, V and VI. In each case, the flavor with the 1-ethynyl-2,2,6-trimethyl-cyclohexanol has an earthy note characteristic of and required for a baked potato flavor; missing in the basic formulation. This earthy note is present both in aroma and taste and makes the taste fuller and more baked potato-like. Therefore a bench panel of four members preferred unanimously the flavor with the 1-ethynyl-2,2,6-trimethyl-cyclohexanol.

EXAMPLE VIII

USE OF β-DAMASCONE IN BASIC RASPBERRY FORMULATION

The following formulation is prepared:

| Ingredients | Parts by Weight |
| --- | --- |
| Vanillin | 5 |
| Maltol | 5 |
| Parahydroxy phenyl butanone | 5 |
| Alpha-ionone (10% in food grade ethanol) | 2 |
| Ethyl butyrate | 16 |
| Dimethyl sulfide | 1 |
| Isobutyl acetate | 16 |
| Ethyl acetate | 20 |
| Acetic acid | 20 |
| Acetaldehyde | 10 |
| Propylene glycol | 900 |

The basic raspberry flavor is compared at the rate of 100 ppm in water with and without the addition of 0.01% β-damascone prepared according to Example IV, Step "B". The flavor with the β-damascone has a delicate raspberry juice aroma with the sweet, berry notes characteristic for this particular fruit. The taste is of full ripened raspberries, juicy and delicate. Therefore, a bench panel of five members prefers, unanimously, the flavor with the β-damascone.

EXAMPLE IX

USE OF 1-ETHYNYL-2,2,6-TRIMETHYL-CYCLOHEX-ANOL IN MASHED POTATO FOODSTUFF

Newly prepared mashed potatoes having a temperature of 170° F. are mixed in a blender with 1-ethynyl-2,2,6-trimethyl-cyclohexanol prepared according to Example II. The 1-ethynyl-2,2,6-trimethyl-cyclohexanol is added to the mashed potatoes while maintaining the temperature of same at 150° F., at a rate of 0.15 ppm. The mashed potatoes are augmented in flavor in that they have an intent earthy note which causes the mashed potatoes to be "baked potato-like" rather than bland.

EXAMPLE X

USE OF 1-ETHYNYL-2,2,6-TRIMETHYL-CYCLOHEX-ANOL IN RED BEET 0.5% Solution of acetic acid in water is admixed with 1-ethynyl-2,2,6-trimethyl-cyclohexanol (10% in food grade ethanol) whereby the level of 1-ethynyl-2,2,6-trimethyl-cyclohexanol in the acetic acid is 0.05%. The resulting acetic acid-1-ethynyl-2,2,6-trimethylcyclohexanol is then added to sliced red beet in the ratio of 0.25 parts vinegar composition:1 part red beet. After permitting the red beet to marinate in a refrigerator (at 0° C. or 32° F.) for a period of four hours, the red beets are tasted and are considered by a bench panel to have a natural fresh-picked red beet character as opposed to "canned red beet character" of the sliced beets prior to addition of the acetic acid composition. The same results are obtained when the level of 1-ethynyl-2,2,6trimethyl-cyclohexanol in vinegar is at 0.2%, 0.25%, 0.3%, and 0.5%. The same results are obtained when the ratio of acetic acid composition:red beets varies from 0.15 parts acetic acid composition:1 part red beet up to 1 part acetic acid composition:1 part red beet.

What is claimed is:

1. The process for augmenting or enhancing the aroma or taste of a foodstuff comprising adding to said foodstuff from 0.02 parts per million up to about 500 parts per million based on said foodstuff of the compound having the structure:

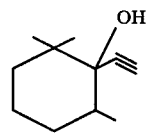

* * * * *